United States Patent [19]

Crews et al.

[11] Patent Number: 4,959,370

[45] Date of Patent: Sep. 25, 1990

[54] ALKALOIDS OF MARINE ORIGIN

[76] Inventors: Phillip Crews, 7777 Monterey St., Santa Crux, Calif. 95060; Thomas R. Matthews, 1579 Hidden Hill Pl., Los Gatos, Calif. 95030; Wayne D. Inman, 11591 Lake Blvd., Felton, Calif. 95018

[21] Appl. No.: 330,164

[22] Filed: Mar. 29, 1989

[51] Int. Cl.$^5$ .................... A61K 31/44; C07D 471/16
[52] U.S. Cl. ........................................ 514/280; 546/48
[58] Field of Search ........................... 546/48; 514/279

[56] References Cited

U.S. PATENT DOCUMENTS 4,868,191  9/1989  Komota et al. ..................... 514/280

OTHER PUBLICATIONS

N. M. Cooray et al, J. Org. Chem. (1988) 53:4619–4620.
G. P. Gunawardana et al, J. Am. Chem. Soc. (1988) 110:4856–4858.
J. Kobayashi et al, Tetraderon Lett. (1988) 29:1177–1180.
T. F. Molinsky et al, J. Org. Chem. (1988) 53:1340–1341.
A. Rudi et al, Tetrahedron Lett. (1988) 31:3861–3962.
S. J. Bloor et al, J. Am. Chem. Soc. (1987) 109:6134–6136.
G. Climino et al, Tetrahedron (1987) 43:4023–4330.
F. J. Schmitz et al, J. Am. Chem. Soc. (1983) 105:4835–4836.

Primary Examiner—Mark L. Berch
Assistant Examiner—Celia Chang
Attorney, Agent, or Firm—Irell & Manella

[57] ABSTRACT

This invention is directed to novel compounds of Formula (I):

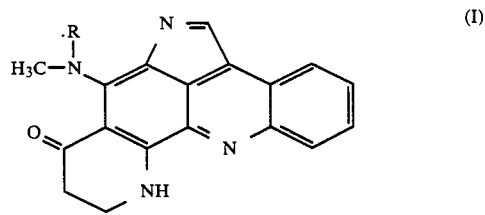

wherein R is hydrogen or methyl, or a pharmaceutically acceptable salt thereof and pharmaceutical compositions formulated therewith. This invention is also directed to a method for treating helminthiasis and for inhibiting reverse transcriptase activity in an animal by the administration of compounds of Formula (I).

11 Claims, No Drawings

ALKALOIDS OF MARINE ORIGIN

STATEMENT OF GOVERNMENT INTEREST

This invention was made with Government support under the National Sea Grant College Program, project number R/MP-41 awarded by the National Oceanic and Atmospheric Administration.

BACKGROUND OF THE INVENTION

1. Field Of the Invention

This invention relates to novel pentacyclic aromatic alkaloids of marine origin and their use as anthelmintics and inhibitors of reverse transcriptase activity. This invention also relates to pharmaceutical compositions formulated therewith.

2. Related Disclosures

Many polycyclic aromatic alkaloids, most of which exhibit a variety of biological activities, have been isolated from marine plants and animals. See, for example, the following:

(a) "Shermilamine A: A Pentacyclic Alkaloid from a Tunicate," P. J. Scheuer et al., *Journal of Organic Chemistry* 1988, Vol. 53, pp. 4619–4620, where the isolation and structure elucidation of a marine invertebrate-derived thiazinone-containing pentacyclic alkaloid is described;

(b) "A Novel Pentacyclic Aromatic Alkaloid from an Ascidian," F. J. Schmitz et al., *Journal of the American Chemical Society* 1987, Vol. 109, No. 20, pp. 6134–6136, where the isolation of a fused pentacyclic aromatic alkaloid is described;

(c) "Ascididemin, A Novel Pentacyclic Aromatic Alkaloid with Potent AntiLeukemic Activity From the Okinawan Tunicate Didemnum Sp.," J. Kobayashi et al., *Tetrahedron Letters* 1988, Vol. 29, No. 10, pp. 1177–1180, where the isolation and structure elucidation of a novel pentacyclic aromatic alkaloid having potent antineoplastic activity is described;

(d) "Amphimedine, New Aromatic Alkaloid from a Pacific Sponge, Amphimedon sp. Carbon Connectivity Determination from Natural Abundance $^{13}C$—$^{13}C$ Coupling Constants," F. J. Schmitz et al., *Journal of the American Chemical Society* 1983. Vol. 105, No. 14, pp. 4835–4836, where a new, cytotoxic fused pentacyclic aromatic alkaloid of marine origin is described;

(e) "Petrosamine, a Novel Pigment from the Marine Sponge Petrosia sp.," T. F. Molinski et al., *Journal of Organic Chemistry* 1988, Vol. 53, pp. 1341–1343, where a new alkaloid of marine origin, similar to amphimedine, is described;

(f) "Dercitin, a New Biologically Active Acridine Alkaloid from a Deep Water Marine Sponge, Dercitus sp.," O. J. McConnell et al., *Journal of the American Chemical Society* 1988, Vol. 110, No. 14, pp. 4856–4858, where the structure elucidation of a fused Pentacyclic aromatic alkaloid of marine origin is described., (g) "Alkaloid Metabolites of the Marine Tunicate Eudistoma sp.: Segoline A, Isosegoline A and Norsegoline," Y. Kashman et al., *Tetrahedron Letters* 1988, Vol. 29, No. 31, pp. 3861–3862, where the structure elucidation of several polycyclic alkaloids is described; and (h) "Studies on the Structure of Calliactine, the Zoochrome of the Sea Anemone *Calliactis Parasitica*," C. Cimino et al., *Tetrahedron* 1987, Vol. 43, No. 17, pp. 4023–4030, where the structure elucidation of a pentacyclic aromatic alkaloid is described.

The disclosure of these and all other documents referred to in this specification are incorporated herein by reference.

SUMMARY OF THE INVENTION

This invention involves the extraction and structure elucidation of novel pentacyclic aromatic alkaloids, referred to herein as "plakinidine A and plakinidine B," from a Vanuatuan red sponge in the genus Plakortis. The carbon skeleton of these alkaloids represents a structural variation not previously reported in aromatic alkaloids of marine organisms. Both plakinidines exhibit anthelmintic activity when administered to animals. In addition, plakinidine A inhibits reverse transcriptase activity in animals when administered thereto.

Therefore, one aspect of the invention is the compound of Formula (I):

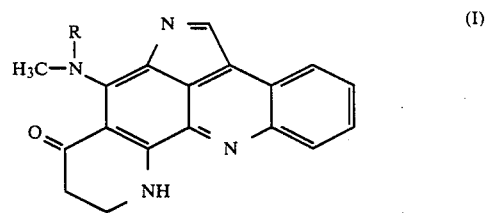

wherein R is hydrogen or methyl, or a pharmaceutically acceptable salt thereof.

Another aspect of the invention is the method for treating helminthiasis in an animal, which method comprises administering to an animal in need thereof an anthelmintically effective amount of a compound of Formula (I).

Another aspect of the invention is a composition for treating helminthiasis in an animal which composition comprises an anthelmintically effective amount of a compound of Formula (I) or a pharmaceutically acceptable salt thereof, and a pharmaceutically acceptable excipient.

Another aspect of the invention is a method for inhibiting reverse transcriptase activity in animal cells which method comprises administering to an animal in need thereof an inhibitory amount of the compound of Formula (I) wherein R is hydrogen, or a pharmaceutically acceptable salt thereof.

Another aspect of the invention is a composition for inhibiting reverse transcriptase activity in animal cells which composition comprises an inhibitory effective amount of the compound of Formula (I) wherein R is hydrogen or a pharmaceutically acceptable salt thereof, and a pharmaceutically acceptable excipient.

DETAILED DESCRIPTION OF THE INVENTION

Definitions

As used in the specification and appended claims, unless specified to the contrary, the following terms having the meaning indicated:

The term "plakinidine" refers to a compound of the Formula (I):

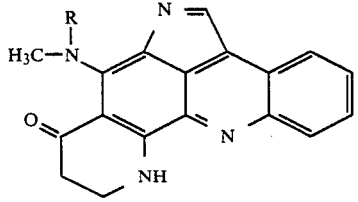

(I)

wherein R is hydrogen or methyl, or a pharmaceutically acceptable salt thereof.

The term "plakinidine A" refers to the compound of Formula (I) wherein R is hydrogen.

The term "plakinidine B" refers to the compound of Formula (I) wherein R is methyl.

The term "reverse transcriptase activity" refers to the action of an enzyme, reverse transcriptase, that is unique to retroviruses, such as Human Immunodeficiency Virus type one (HIV-1). The propagation of retroviruses depends on the activity of this enzyme, which constructs DNA from viral RNA. Thus, the inhibition of reverse transcriptase activity may prevent propagation of the virus.

The term "pharmaceutically acceptable" as used herein includes that which is acceptable for veterinary use, and is not limited to suitability for human use.

The term "pharmaceutically acceptable salt" refers to salt of the subject compounds which possesses the desired pharmacological activity and which is neither biologically nor otherwise undesirable. This salt is an acid addition salt formed with inorganic acids such as hydrochloric acid, hydrobromic acid, sulfuric acid, nitric acid or phosphoric acid; or organic acids such as acetic acid, propionic acid, glycolic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p toluenesulfonic acid and the like.

The term "animal" includes humans and all domestic and wild mammals and fowl, including, without limitation, cattle, horses, swine, sheep, goats, dogs, cats, rabbits, deer, mink, chickens, ducks, geese, turkeys, game hens, and the like.

The term "treatment" as used herein covers any treatment of a disease in an animal and includes:

(i) preventing the disease from occurring in an animal which may be predisposed to the disease but has not yet been diagnosed as having it;

(ii) inhibiting the disease, i.e., arresting its development; or (iii) relieving the disease, i.e., causing regression of the disease.

The term "anthelmintically effective amount" refers to that amount which, when administered to an animal in need thereof, is sufficient to effect treatment, as defined above. Furthermore, an "anthelmintically effective amount" of a compound of Formula (I) for treating helminthiasis will vary depending on the species of helminth, the severity of the infection, and the animal to be treated, but may be determined routinely by one of ordinary skill in the art.

The term "inhibitory effective amount" refers to that amount which, when administered to an animal in need thereof, is sufficient to inhibit reverse transcriptase activity, as defined above. Furthermore, an "inhibitory amount" of a compound of Formula (I) for treating viral infections will vary depending on the virus, the severity of the infection, and the animal to be treated, but may be determined routinely by one of ordinary skill in the art.

Preferred Embodiments

One aspect of the invention is the compound of Formula (I):

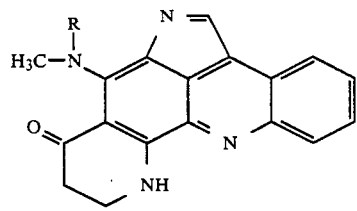

(I)

wherein R is hydrogen or methyl, or its pharmaceutically acceptable salts. A presently preferred embodiment of the invention is the compound of Formula (I) wherein R is hydrogen that is at least 90% pure, preferably at least 95% pure, and most preferably at least 99% pure. Another presently preferred embodiment of the invention is the compound of Formula (I) wherein R is methyl that is at least 90% pure, preferably at least 95% pure, and most preferably at least 99% pure.

Methods of Extraction:

The compounds of Formula (I) can be extracted from a Vanuatuan marine sponge, tentatively identified as being in the genus Plakortis (order Homosclerophorida; family Plakinidae Schulze, 1880). The sponge has the following characteristics, by which one of ordinary skill in the art may recognize the appropriate sponge and distinguish it from others:

The Plakortis species sponge can be found approximately thirty feet below the surface of Melé Bay of the island of Efaté, Vanuatu. The sponge can be massive and amorphous in shape. The sponge is red when alive and brick red when dried. Its ectosome is detachable and pierced by regularly spaced pores that are approximately 20 $\mu$m in diameter. Its choanosome is massive and exhibits a compact arrangement of various spicules.

A fresh Plakortis so. sponge, collected from Melé Bay, is cut into small pieces and immersed in $CH_2Cl_2$ for 24 hours. The $CH_2Cl_2$ is then decanted. The sponge is next soaked with MeOH for 24 hours. Afterwards, the MeOH is decanted and combined with the $CH_2Cl_2$. The solvents are then evaporated to yield a crude oil. The oil is successively partitioned between equal volumes of methanol (wet, percent adjusted to produce a biphase solution) and a solvent series of hexanes (B), $CCl_4$ ($\alpha$), $CH_2Cl_2$ ($\beta$). The $\alpha$ and $\beta$ partition fractions were then column chromatographed (reverse phase and Sephadex LH 20). The compound of Formula (I) wherein R is hydrogen, i.e., plakinidine A, was isolated as a deep purple solid from methanol while the compound of Formula (I) wherein R is methyl, i.e., plakinidine B, was isolated as a purple oil. The purple color of these extracts changes according to the pH, thereby being reminiscent of hue fluctuations recently observed for other polycyclic aromatic alkaloids of marine origin.

The structure of the compounds of Formula (I) was elucidated as follows:

The molecular formula of the compound of Formula (I) wherein R is hydrogen, plakinidine A, was determined to be $C_{18}H_{14}N_4O$ from HREIMS m/z 302.1169 (M+, $\Delta$ 0.1 mmu of calc.) and an APT $^{13}$C NMR spectrum. COSY experiments in DMSO-$d_6$ and $CDCl_3$-

TFA-d (1:1) identified four separate proton spin systems. The NMR data is summarized in the following TABLE 1 and TABLE 2:

TABLE 1

¹H and ¹³C NMR Data for Plakinidine A in CDCl₃/TFA-d (1:1).

| Atom # | δH at C | Multiplicity, $^3J_{H-H}$ (Hz) | H coupled with H | δC |
|---|---|---|---|---|
| 2 | 8.84 | s | | 127.4 |
| 2a | | | | 125.76 |
| 2b | | | | 125.84 |
| 3 | 8.64 | d,7.8 | H-4 | 125.3 |
| 4 | 8.23 | t,6.9 | H-3,H-5 | 135.3 |
| 5 | 8.17 | t,7.2 | H-4,H-6 | 133.7 |
| 6 | 8.71 | d,8.4 | H-5 | 124.2 |
| 6a | | | | 135.8 |
| 7a | | | | 136.7 |
| 7b | | | | 153.7 |
| 9 | 4.24 | t,7.5 | H-10 | 41.2 |
| 10 | 3.10 | t,7.5 | H-9 | 34.3 |
| 11 | | | | 196.9 |
| 11a | | | | 101.0 |
| 12 | | | | 152.7 |
| 12a | | | | 115.5 |
| 12b | | | | 120.1 |
| 14 | 3.84 | s | | 34.3 |

| Atom # | $^1J_{C-H}$ (Hz) | $^3J_{C-H}$ (Hz) | H coupled with C |
|---|---|---|---|
| 2 | 200.4 | | |
| 2a | | | H-3 |
| 2b | | | H-2,H-4,H-6 |
| 3 | 167.1 | 6.9 | H-5 |
| 4 | 167.2 | 6.9 | H-6 |
| 5 | 168.1 | 7.6 | H-3 |
| 6 | 168.0 | 6.4 | H-4 |
| 6a | | | H-3,H-5 |
| 7a | | | |
| 7b | | | H-9 |
| 9 | 146.6 | | H-10 |
| 10 | 133.2 | | H-9 |
| 11 | | | H-9,H-10 |
| 11a | | | H-10 |
| 12 | | | H-14 |
| 12a | | | H-2 |
| 12b | | | H-2 |
| 14 | 141.8 | | |

TABLE 2

¹H and ¹³C NMR Data for Plakinidine A in DMSO-d₆

| Atom # | δH at C | Multiplicity, $^3J_{H-H}$ (Hz) | H coupled with H | δC |
|---|---|---|---|---|
| 2 | 8.47 | s | | 136.0 |
| 2a | | | | 124.38* |
| 2b | | | | 124.44* |
| 3 | 8.42 | d,7.8 | H-4 | 123.8 |
| 4 | 7.73 | t,7.2 | H-3,H-5 | 128.1 |
| 5 | 7.69 | t,9.3 | H-4,H-6 | 126.2 |
| 6 | 8.27 | d,8.1 | H-5 | 130.3 |
| 6a | | | | 144.1 |
| 7a | | | | 138.1 |
| 7b | | | | 157.9 |
| 8 | 9.93 | bs | H-9 | |
| 9 | 3.82 | dt,7.8,1.2 | H-8,H-10 | 38.0 |
| 10 | 2.72 | t,7.8 | H-9 | 35.5 |
| 11 | | | | 194.0 |
| 11a | | | | 100.0 |
| 12 | | | | 152.0 |
| 12a | | | | 122.3 |
| 12b | | | | 127.7 |
| 13 | 11.17 | q,5.4 | H-14 | |
| 14 | 3.68 | d,5.7 | H-13 | 33.7 |

| Atom # | $^1J_{C-H}$ (Hz) | $^3J_{C-H}$ (Hz) | H coupled with C |
|---|---|---|---|
| 2 | 184.1 | | |
| 2a | | | |
| 2b | | | H-2,H-4,H-6 |
| 3 | 167.1 | 5.5 | H-5 |
| 4 | 160.1 | 8.2 | H-6 |
| 5 | 160.7 | 9.1 | H-3 |
| 6 | 167.0 | 7.0 | H-4 |
| 6a | | | H-3,H-5 |
| 7a | | | |
| 7b | | | H-9 |
| 8 | | | |
| 9 | 141.5 | | H-10 |
| 10 | 131.0 | | H-9 |
| 11 | | | H-9,H-10 |
| 11a | | | H-10,H-13 |
| 12 | | | H-13,H-14 |
| 12a | | | H-13 |
| 12b | 11.7 | | H-2 |
| 13 | | | |
| 14 | 139.5 | | |

*interchangeable

The protons on C-3 to C-6 were on contiguous atoms of an o-disubstituted benzene ring, protons on N-8 to C 10 were part of a —CH2CH2N(H)—group, and the amino proton, H-13, and methyl protons, H-14, composed a —N(H)Me appendage. The remaining proton, H-2, was a low field singlet (δ8.84) with a large $^1J_{CH}$ coupling (200.4 Hz in CDC13/TFA-d) indicating a geminal nitrogen attachment. (Proton effects on the ¹³C δ's and $^1J_{CH}$'s are well known for aromatic nitrogen heterocyclics. Typical J and δ changes at the position α to N (unprotonated versus protonated for pyridine) are respectively +13 Hz and −21 ppm. See, H. Seel et al., Journal of the American Chemical Society 1980, Vol. 102, p. 7051.) The remaining C₉N atoms were assumed to comprise five double bonds based on their ¹³C chemical shifts; consequently, this required five rings to be present. Long range ¹H-¹³C COSY experiments were invaluable for building up larger substructures. Intense correlations to disubstituted benzene ring protons, H-3 and H-6, revealed the location of quaternary carbons, C 2a, C 2b and C 6a. The existence of a six-membered ring β-enaminoketone was required by the IR (1624 cm⁻¹) and COSY NMR correlations from H₂-9 and C-7b, and from H₂-10 to C-11 and C-11a. This substructure was expanded to include the enamine attached at C-11a due to long range correlations from H 13 to C-11a, C 12 and C-12a. In turn, C-12a displayed a long range correlation to H-2 and was required to be in the vicinity of the disubstituted imine. Two other long range COSY correlations were observed from H-2 to C 2a and C 12b.

At this point the two six-membered rings and an —N(H)Me— substituent were fully defined as the terminal groups and, based on the collective NMR data, they could be connected as shown in the following Fragment A:

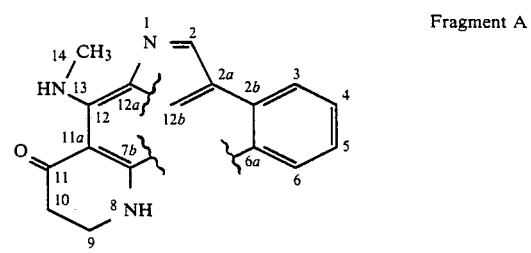

Fragment A

The following Fragment B was needed to be joined to A in order to generate three additional rings:

Fragment B

The nitrogen in Fragment B was joined to C-6a based on the chemical shift of C-6a (δ144.1/DMSO-d6) and dictated the final connections as shown in following FIG. 1.

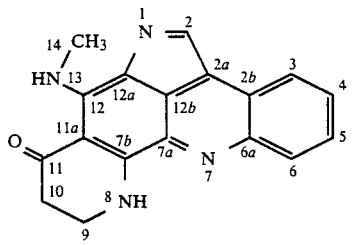

The polyaromatic chromophore of FIG. 1 was consistent with the color and the intense molecular ion observed in the mass spectrum for plakinidine A.

The NMR data for plakinidine B is summarized in the following TABLE 3:

TABLE 3

$^1$H and $^{13}$C NMR Data for Plakinidine B in CDCl$_3$

| Atom # | δH at C | Multiplicity, $^3J_{H-H}$ (Hz) | δC |
|---|---|---|---|
| 2 | 8.49 | s | 137.7 |
| 2a | | | 125.3* |
| 2b | | | 126.9* |
| 3 | 8.32 | dd,8.1,1.5 | 124.1 |
| 4 | 7.67 | dt,6.6,1.2 | 128.3 |
| 5 | 7.61 | dt,6.6,1.2 | 126.5 |
| 6 | 8.19 | dd,8.4,1.2 | 130.5 |
| 6a | | | 144.7 |
| 7a | | | 137.5 |
| 7b | | | 159.5 |
| 8 | 10.05$^a$ | | |
| 9 | 3.77 | dt,6.9,1.8 | 39.3 |
| 10 | 2.71 | t,6.9 | 37.9 |
| 11 | | | 188.2 |
| 11a | | | 106.7 |
| 12 | | | 152.6 |
| 12a | | | 124.9* |
| 12b | | | 129.4 |
| 14a | 3.64$^b$ | bs | 46.2$^c$ |
| 14b | 3.64$^b$ | bs | 46.2$^c$ |

*interchangeable
aδ (ppm) in DMSO-d6.
bδ (ppm) at −40° C.: 3.32, 3.92.
cδ (ppm) at −40° C.: 47.3, 45.0.

From this data, the structure of plakinidine B was elucidated as described above for plakinidine A.

Administration and Formulation

An aspect of the present invention relates to pharmaceutical and veterinary compositions useful in the treatment of helmintic infection, comprising an anthelmintically effective amount of a compound of Formula (I), or a pharmaceutically acceptable acid addition salt thereof, in admixture with a pharmaceutically acceptable excipient. Compounds of Formula (I) are effective against nematodes and other helminths, such as *Nippostrongylus brasiliensis*, at concentrations of about 5 μg/mL to about 250 μg/mL.

Another aspect of the present invention relates to pharmaceutical compositions useful in the inhibition of reverse transcriptase activity in animals, comprising administering to an animal in need thereof an inhibitory amount of the compound of Formula (I) wherein R is hydrogen, or a pharmaceutically acceptable acid addition salt thereof, in admixture with a pharmaceutically acceptable non-toxic carrier.

Useful pharmaceutical excipients for the preparation of the pharmaceutical compositions hereof can be solids, liquids, gels, creams, ointments, and the like. Thus, the compositions can take the form of tablets, pills, capsules, powders, sustained release formulations, solutions, suspensions, elixirs, aerosols, and the like. Carriers can be selected from the various oils, including those of petroleum, animal, vegetable or synthetic origin, for example, peanut oil, soybean oil, mineral oil, seasame oil, and the like. Water, saline, aqueous dextrose, and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monosterarate, sodium chloride, dried skim mile, gylcerol, propylene glycol, water, ethanol, and the like. Other suitable pharmaceutical carriers and their formulations are described in "*Remington's Pharmaceutical Sciences*" by E. W. Martin.

In the practice of the above described method of the present invention an anthelmintically effective amount of the compound of Formula (I) or a pharmaceutical composition containing same is administered via any of the usual and acceptable methods known in the art, either singly or in combination with another compound or compounds of the present invention or other pharmaceutical agents. These compounds or compositions can thus be administered orally or intraruminally, systemically (e.g., transdermally, intranasally or by suppository), topically, or parenterally (e.g., intramuscularly, subcutaneously and intravenously), and can be administered either in the form of solid or liquid dosages including tablets, solutions, suspensions, aerosols, and the like, as discussed in more detail above. It is preferred to administer compounds of Formula (I) orally when treating helminth infestations.

In general, an anthelmintically effective amount of a compound of Formula (I) for the treatment of helminthiasis will range from about 1 to about 100 mg per kilogram body weight per day. Thus, for administration to an animal weighing 200 kg, the dosage range would be about 200 mg to 20 grams per day.

In the practice of the above described method for inhibiting reverse transcriptase activity in animals, an inhibitory effective amount of the compound of Formula (I) wherein R is hydrogen, or a pharmaceutical composition containing same, is administered via any of the usual and acceptable methods known in the art, either singly or in combination with another compound or compounds of the present invention or other pharmaceutical agents. Co-administration can be in the form of a single formulation (combining, for example, a compound of Formula (I) and ganciclovir with pharmaceutically acceptable excipients, optionally segregating the two active ingredients in different excipient mixtures designed to independently control their respective release rates and durations) or by independent administration of separate formulations containing the active agents. These compounds or compositions can thus be administered orally or systemically (e.g., transdermally, intranasally or by suppository), topically, or parenterally (e.g., intramuscularly, subcutaneously and intravenously), and can be administered either in the form of solid or liquid dosages including tablets, solutions, suspensions, aerosols, and the like, as discussed in more detail above.

In general, an inhibitory effective amount of a compound of Formula (I) wherein R is hydrogen is about 0.01 to 150 mg per kilogram body weight of the recipient per day, preferably about 1.5 to 75 mg per kilogram body weight per day, and most preferably about 5 to 30 mg per kilogram body weight per day. Thus, for administration to a 70 kg person, the dosage range would be about 0.7 mg to 10.5 g per day, preferably about 350 mg to 2.1 g per day.

The following specific examples are provided as a guide to assist in the practice of the invention, and are not intended as a limitation on the scope of the invention.

EXAMPLE 1

(Extraction)

A fresh Plakortis sp. sponge, Collected from approximately 30 feet below the surface of Melé Bay on the island of Efaté, Vanuatu, is cut into small pieces and immersed in $CH_2Cl_2$ for 24 hours. The $CH_2Cl_2$ is then decanted. The sponge is next soaked with MeOH for 24 hours. Afterwards, the MeOH is decanted and combined with the $CH_2Cl_2$. The solvents are then evaporated to yield a crude oil (3.87 g). The oil is successively partitioned between equal volumes of methanol (wet, percent adjusted to produce a biphase solution) and a solvent series of hexanes (B), $CCL_4$ ($\alpha$), $CH_2Cl_2$ ($\beta$). The $\alpha$ and $\beta$ partition fractions were then column chromatographed (reverse phase and Sephadex LH-20). The compound of Formula (I) wherein R is hydrogen, i.e., plakinidine A, was isolated as a deep purple solid from methanol (52 mg, 0.026% wet wt., mp. 248°–250° C.). The compound of Formula (I) wherein R is methyl, i.e., plakinidine B, was isolated as a purple oil (24 mg).

EXAMPLE 2

(Formulations)

The following example illustrates the preparation of representative pharmaceutical formulations containing an active compound of Formula (I):

(A) The following formulation is suitable for intravenous administration, oral drench, and (in the treatment of large ruminants) intraruminal injection.

| Formulation | | |
|---|---|---|
| Compound of Formula (I) | | 10.0 g |
| Propylene glycol | | 20.0 g |
| Polyethylene glycol 400 | | 20.0 g |
| Tween ® 80 | | 1.0 g |
| 0.9% Saline solution | qs | 100.0 mL |

The compound of Formula (I) is dissolved in propylene glycol, polyethylene glycol 400 and Tween ® 80. A sufficient quantity of 0.9% saline solution is then added with stirring to provide 100 mL of the I.V. solution which is filtered through a 0.2 micron membrane filter and packaged under sterile conditions.

(B) A tablet formulation is prepared as follows:

| | Parts |
|---|---|
| Compound of Formula (I) | 5.0 |
| Magnesium stearate | 0.75 |
| Starch | 0.75 |
| Lactose | 29.0 |
| PVP (polyvinylpyrrolidone) | 0.75 |

The above ingredients are combined and granulated using methanol. The formulation is then dried and formed into tablets (containing 500 mg of active compound) with an appropriate tabletting machine.

EXAMPLE 4

(In Vitro Anthelmintic Activity)

To obtain the fourth larval stage (L4) of *Nippostrongylus brasiliensis*, rats were inoculated with 6,500 to 6,750 *N. brsiliensis* third stage larvae subcutaneously. Seventy-two hours later the rats were sacrificed and the fourth stage larvae harvested. Compounds of Formula (I) were tested at 50 µg/mL against the fourth larval stage of *N. brasiliensis* at approximately 50 L4/well. This mixture was incubated at 37° C. for a total of seven days and then read for activity. Parameters used to determine drug activity were motility, viability, and the ability of fourth stage larvae to molt to the adult, i.e., cast formation. A compound was defined as active if (1) cast formation was reduced by 40 percent or more; or (2) viability and motility together were reduced 40 percent or more.

The results are illustrated in the following Table I:

TABLE 1

| | PERCENT REDUCTION COMPARED TO CONTROL | | | |
|---|---|---|---|---|
| Compound | Conc. | Casts* | Viability** | Motility*** |
| Compound A | 50 µg/ml | 100% | 100% | 100% |
| Compound B | 50 µg/ml | 100% | 100% | 100 |

Compound A is a compound of Formula (I) where R is hydrogen.
Compound B is a compound of Formula (I) where R is methyl. *Percent cast reduction was determined by the following:
$$\frac{\text{No. of untreated casts} - \text{No. of casts}}{\text{No. of untreated casts}} \times 100$$
**Percent viability reduction was determined by the following:
$$\frac{\text{No. of untreated worms} - \text{No. of worms}}{\text{No. of untreated worms}} \times 100$$
***Percent motility reduction was a subjective evaluation

EXAMPLE 5

(In Vitro Reverse Transcriptase Inhibitory Activity)

The activity of purified cloned reverse transcriptase (RT), in the presence or absence of test compound, was assayed by measuring the incorporation of tritiated thymidine triphosphate ([$^3$H] TTP) into a DNA chain using polyadenosine as the template and oligodeoxythymidine as the primer (*Biochem. Pharm.* 1987, Vol. 36, No. 24 pp. 4361–4362). The final concentration of the compounds tested for anti-RT activity was 400 µg/ml in 10 percent DMSO. Controls contained 10 percent DMSO only. After incubation at 37° C. for 0, 15, and 30 minutes, an aliquot of the incubation mixture was spotted on cellulose paper, washed in TCA-pyrophosphate solution to remove [$^3$H] TTP, dried and analyzed for the rate of incorporation of radioactivity. The compounds which inhibited more than 50 percent of the enzyme activity, as determined by a decrease in radioactivity compared with controls, were considered active. The compound of Formula (I) where R is hydrogen exhibited 83% inhibition.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of Formula (I):

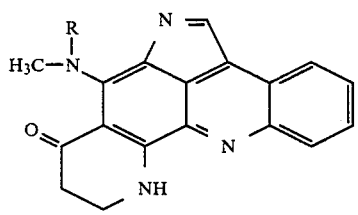

wherein R is hydrogen or methyl, or a pharmaceutically acceptable salt thereof.

2. The compound of claim 1 wherein R is hydrogen.
3. The compound of claim 1 wherein R is methyl.
4. A method for treating helminthiasis which method comprises administering to an animal in need thereof an anthelmintically effective amount of a compound of Formula (I):

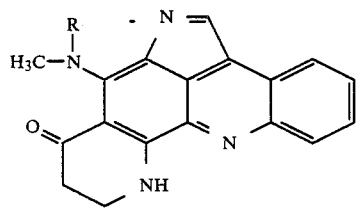

wherein R is hydrogen or methyl, or a pharmaceutically acceptable salt thereof.

5. The method of claim 4 wherein R is hydrogen.
6. The method of claim 4 wherein R is methyl.

7. A composition for treating helminthiasis in an animal which composition comprises an anthelmintically effective amount of a compound of Formula (I):

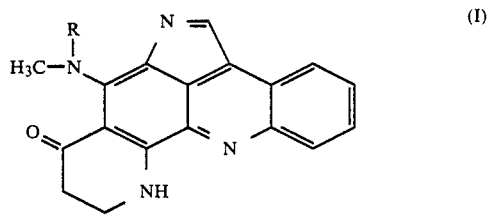

wherein R is hydrogen or methyl, or a pharmaceutically acceptable salt thereof; and a pharmaceutically acceptable excipient.

8. The composition of claim 7 wherein R is hydrogen.
9. The composition of claim 7 wherein R is methyl.
10. A method for inhibiting reverse transcriptase activity in animal cells which method comprises administering to an animal in need thereof an inhibitory amount of the compound:

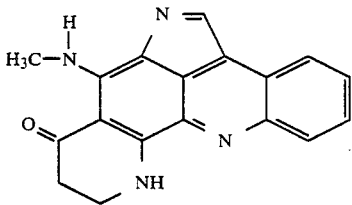

or a pharmaceutically acceptable salt thereof.

11. A composition for inhibiting reverse transcriptase activity in animal cells which composition comprises an inhibitory effective amount of the compound:

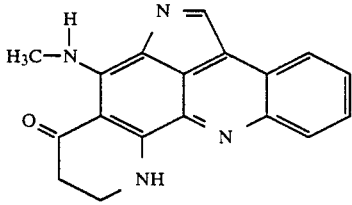

or a pharmaceutically acceptable salt thereof, and a pharmaceutically acceptable excipient.

* * * * *